United States Patent [19]

Gleason et al.

[11] Patent Number: 5,140,861
[45] Date of Patent: Aug. 25, 1992

[54] MULTIFUNCTION TABLET TESTER

[75] Inventors: David D. Gleason, Kalamazoo; Larry R. Carter, Richland; P. Timothy Frey, Delton, all of Mich.

[73] Assignee: The Upjohn Company, Kalamazoo, Mich.

[21] Appl. No.: 695,432

[22] Filed: May 3, 1991

[51] Int. Cl.⁵ .......................... G01N 3/40; G01N 3/56
[52] U.S. Cl. ........................ 73/865.8; 73/7; 73/81
[58] Field of Search .............. 73/7, 81, 82, 818, 865.8, 73/866

[56] References Cited

U.S. PATENT DOCUMENTS

| | | | |
|---|---|---|---|
| 3,128,621 | 4/1964 | Scott | 73/81 |
| 3,255,716 | 6/1966 | Knoechell et al. | 73/818 |
| 3,915,651 | 10/1975 | Nishi | 73/864.16 |
| 4,094,188 | 6/1978 | Bellouin et al. | 73/81 |
| 4,462,245 | 7/1984 | Gould et al. | 73/7 |
| 4,481,814 | 11/1984 | Wentzell | 73/866.5 |
| 4,535,623 | 8/1985 | Gilberto | 73/81 |
| 4,542,646 | 9/1985 | Smith et al. | 73/78 |
| 4,608,854 | 9/1986 | Vandermeerssche | 73/7 |
| 4,633,712 | 1/1987 | Scieszka | 73/7 |
| 4,658,631 | 4/1987 | Swon | 73/7 |
| 4,875,363 | 10/1989 | Hinduja et al. | 73/866 |
| 4,880,373 | 11/1989 | Balog et al. | 425/149 |
| 4,885,933 | 12/1989 | Hiestand et al. | 73/79 |
| 4,957,003 | 9/1990 | Hiestand et al. | 73/818 |
| 5,044,193 | 9/1991 | Fudacz | 73/818 |

*Primary Examiner*—Robert Raevis
*Assistant Examiner*—Howard Wisnia
*Attorney, Agent, or Firm*—Flynn, Thiel, Boutell & Tanis

[57] ABSTRACT

An apparatus for testing several physical properties of pharmaceutical powders, which apparatus includes a frame having a ram linearly movably supported thereon and driven from a microstepping rotary drive motor. The ram, through a first load cell, cooperates with a selected one of two different tablet supporting head assemblies which removably mount of the frame for respectively testing tablet hardness and tensile strength. The frame also mounts a powder flow test arrangement which includes a bed stationarily supported on the frame for receiving a layer of powder, and a sled which rests on the powder layer and is freely horizontal movable relative to the bed. The sled is coupled through a generally horizontal tension member to a second load cell which is mounted on the ram independently of the first load cell.

18 Claims, 6 Drawing Sheets

MULTIFUNCTION TABLET TESTER

FIELD OF THE INVENTION

This invention relates to a multifunction tablet tester for running several different tests to determine tableting properties of powders or particulate materials, particularly pharmaceutical powders.

BACKGROUND OF THE INVENTION

In the pharmaceutical industry, it is important to know the parameters which characterize the tableting properties of powders which are compressed to form tablets used for human and animal consumption. It is desirable to have a method of quantitatively evaluating the tableting characteristics of a powder before it is mixed with other materials so as to permit detection and rejection of lots that, if used, would introduce problems such as capping or excessive friability. Such methods are also useful to assist in formulating new chemical entities. By being able to initially define what tableting indices are critical, and then by being able to experimentally measure such indices based on tablets or compacts formed from test samples, the need for formulation of large samples and the control and predictability of the tableting performance can be much more reliability controlled and achieved.

It is believe that the bonding index of the powder is probably the most important parameter, and it has been determined that the bonding index itself involves two tableting indices, these being referred to as the best and worst case indices. The difference between the best case and worst case boding indices indicates whether the material is viscoelastic. In the final formulation of the powder viscoelastic, it will be sensitive to the rate that the tableting machine is run, that is, to the strain rate. However, viscoelasticity promotes stronger bonding. Thus, qualitative evaluation of the difference between these best and worst case bonding indices is highly desirable.

An evaluation of the bonding index involves application of a compressive force to a surface of a compact (i.e., a blocklike tablet of compressed powder). This involves creation of a partial spherical indentation in the surface of the compact to permit a hardness value to be determined.

To experimentally determine the worst case bonding index, it is typical to use a procedure whereby a steel ball or sphere is bounded off a surface of the compact, whereby the steel ball creates a partial spherical depression in the compact. The steel ball, upon impact against the surface of the compact, imposes a compressive load on the compact, and the mean pressure under the ball is an indication of the shear strength of the compact under compressive load. This permits determination of the worst case bonding index. A desirable pendulum-type impact tester for this purpose is illustrated by U.S. Pat. No. 4,885,933, owned by the Assignee hereof.

To obtain a hardness which corresponds to the best case bonding index, however, requires the use of a procedure which creates a very slow effective strain rate when compressive load is imposed on the compact, such as by means of a sphere. Such an apparatus is disclosed in U.S. Pat. No. 4,957,003, owned by the Assignee hereof.

The determination of the worst case bonding index also involves a determination of a slow strain rate tensile strength measurement of a compact. This is created by slowly imposing a compressive load on the compact as it is held between opposed and relatively movable platens until the compact fails. This permits measurement of the slow strain rate tensile strength of the compact. An apparatus used for this purpose is also illustrated by aforementioned U.S. Pat. No. 4,957,003.

While the apparatus disclosed by aforementioned U.S. Pat. No. 4,957,003 has been successfully utilized to permit more accurate evaluation of the tableting properties of pharmaceutical powders, nevertheless the testing accuracy resulting from use of this known apparatus is less than desired and hence does not always provide the desired degree of accuracy, reliability and repeatability, particularly since such tests may be conducted at numerous different locations at significantly different times. In particular, it has been discovered that the known apparatus, which utilizes continuous rotation of an AC or DC motor as a driving source, cannot be made to perform with the required or desired degree of control both with respect to speed and displacement of the force-producing ram. The inertia of the drive arrangement is such as to effectively prevent precise control over the indentation of the ball into the tablet, and likewise prevents precise measurement of the force/displacement characteristics upon failure of the tablet during the slow strain rate tensile strength measurement test.

Another test which has been used for evaluating the tableting properties of pharmaceutical powders is normally referred to as the shear cell test. In this procedure, a thin layer of powder is positioned between two opposed rough surfaces, the lower defining a bed, and the upper defining a sled which is movable horizontally along the powder layer. The sled is coupled through a flexible tow line and a force transducer to a linear driver, the latter being driven from a conventional continuous-rotation AC or DC motor via a suitable gear drive. The sled has a horizontal towing force applied thereto and, as the layer of powder undergoes a state of consolidation, the force applied to the sled is effective in overcoming the frictional powder force to movably displace the sled along the powder layer. This test is conducted in a repeated manner to generate a strain gauge output which is of a saw tooth pattern which raises as the pressure builds and then drops substantially to zero as the powder shear is exceeded. In this manner values of powder shear or. flow can be determined. However, the known apparatus for conducting this test possesses similar disadvantages in that the driving ram possesses undesirable inertia and coasting due to the overall drive arrangement, and thus carrying out tests in a highly controlled and precise manner while simultaneously recording precise experimental results is generally not achievable.

Accordingly, it is an object of the present invention to provide an improved multifunction apparatus for testing the properties of pharmaceutical powders so as to permit several different tests to be conducted thereon to permit determination of different properties of the pharmaceutical powders, which tests can be conducted with a high degree of accuracy and reliability so that the test results are not subject to errors caused by poor quality or excessive tolerances associated with the testing apparatus or caused by the mechanical structure and/or inertia associated with the drive arrangement.

More specifically, in the improved multifunction testing apparatus of the present invention, there is provided a slidable ram which cooperates with at least three different test assemblies to permit multiple testing functions to be carried out, such as powder flow determination, tensile strength, and slow strain rate hardness (often referred to as quasi-static hardness). This improved multifunction testing apparatus includes a precision microstepping motor which can be controlled to provide for an extremely large number of steps per rotation, which motor in turn is suitably coupled to the ram, as through a precision nut-screw arrangement, to provide for precise control over both the velocity and linearly displacement of the ram. This enables the ram to be moved through precise small increments, which increments occur at an extremely high rate so that the movement of the ram approaches a linear velocity, but at the same time the velocity and ram displacement can be accurately positioned by controlling the rotational steps of the driving motor. Thus, accurate experimental results can be recorded from suitable force transducers which are coupled to the ram when the apparatus is used for conducting various ones of the three described tests.

In a preferred embodiment, the ram has a high-capacity force transducer associated therewith, and an indentation ball or platen is removably couple thereto for cooperation with either a quasi-static hardness test assembly or a tensile strength assembly, which assemblies interchangeably mount on the test apparatus. The ram is also coupled to a second low-force transducer which can be coupled to a sled when a powder flow test is to be conducted. Outputs from the transducer are preferably fed directly to a computer and/or a recording device (such as an oscilloscope). The computer is also suitably programmed to provide for precise control of the stepping motor to control the physical test parameters, such as the velocity and displacement of the ram.

Other objects and purposes of the present invention will be apparent to persons familiar with arrangements of this general type upon reading the following specification and inspecting the accompanying drawings.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the apparatus and designated parts thereof. Said terminology will include the words specifically mentioned, derivatives thereof, and words of similar import.

DETAILED DESCRIPTION

Figure 1:
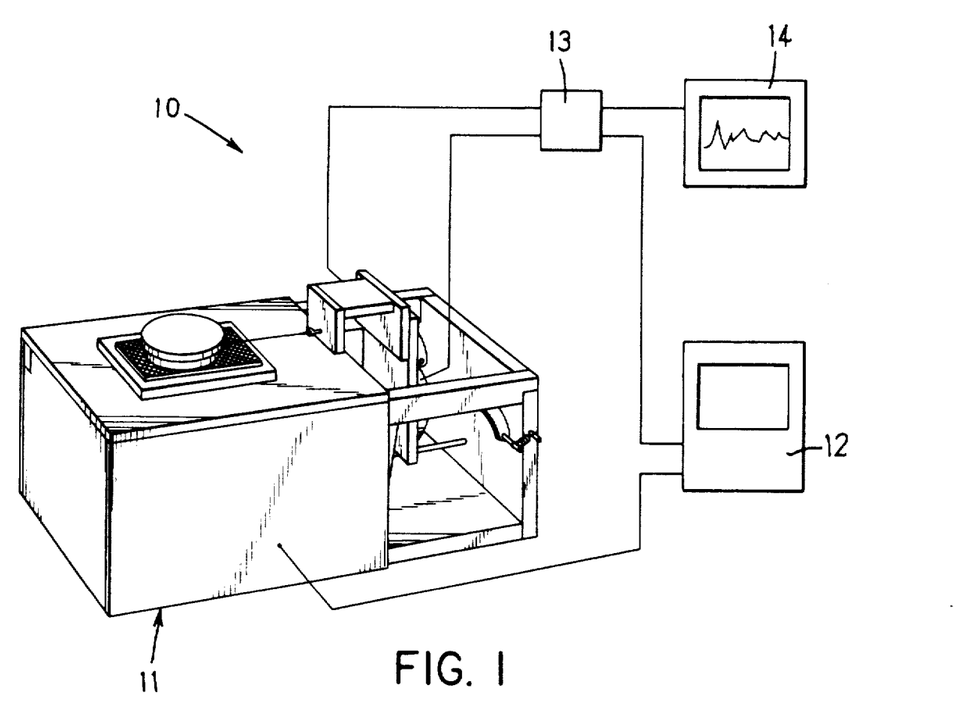
FIG. 1 is a perspective view of a multifunction tester for pharmaceutical powders and diagrammatically illustrates the connection of the loading module to a computer and a plotting or display arrangement.

Referring to FIG. 1, there is illustrated a testing apparatus 10 including a load module 11 which is preferably controlled by a computer 12. Output signals from the module 11, such as from suitable force transducers therein, are transmitted to a suitable junction box 13 which in turn permits selection of the signals and feeding thereof to the computer 12 and/or to a recording device 14 such as an oscilloscope.

Figure 2:
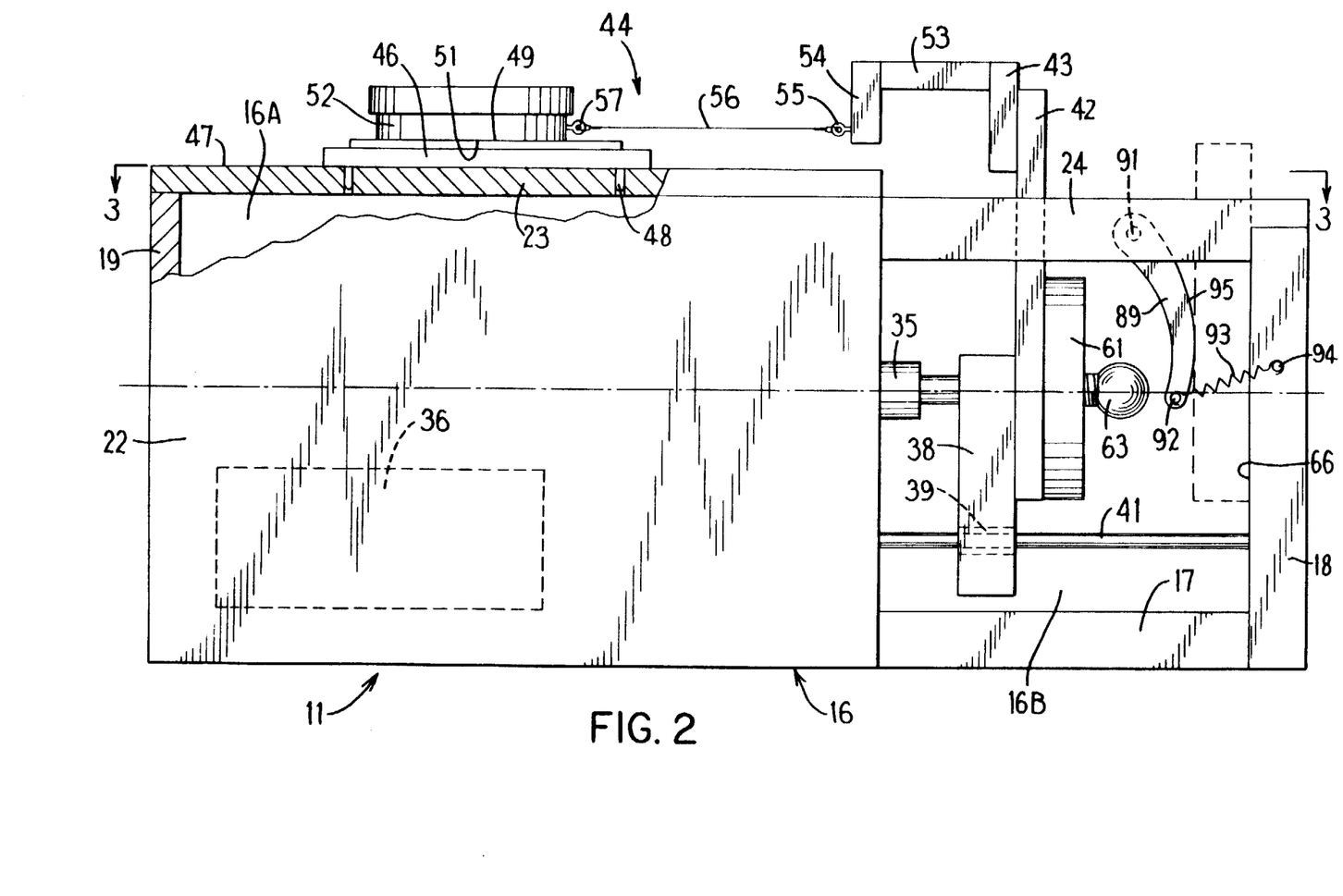
FIG. 2 is a side elevation view of the load module.
Figure 3:
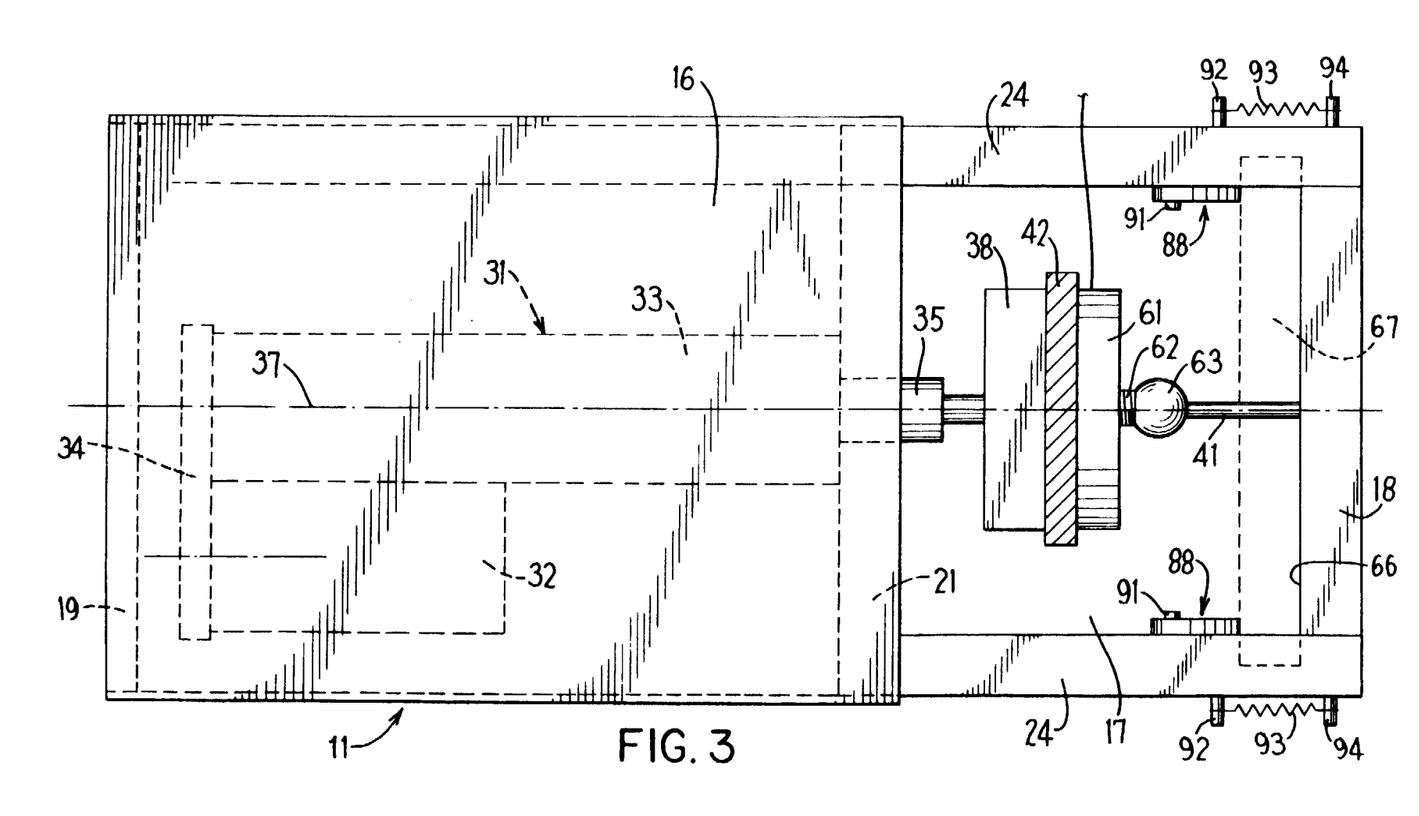
FIG. 3 is a top view of the load module as taken substantially along line 3—3 in FIG. 2.
Figures 4, 5:
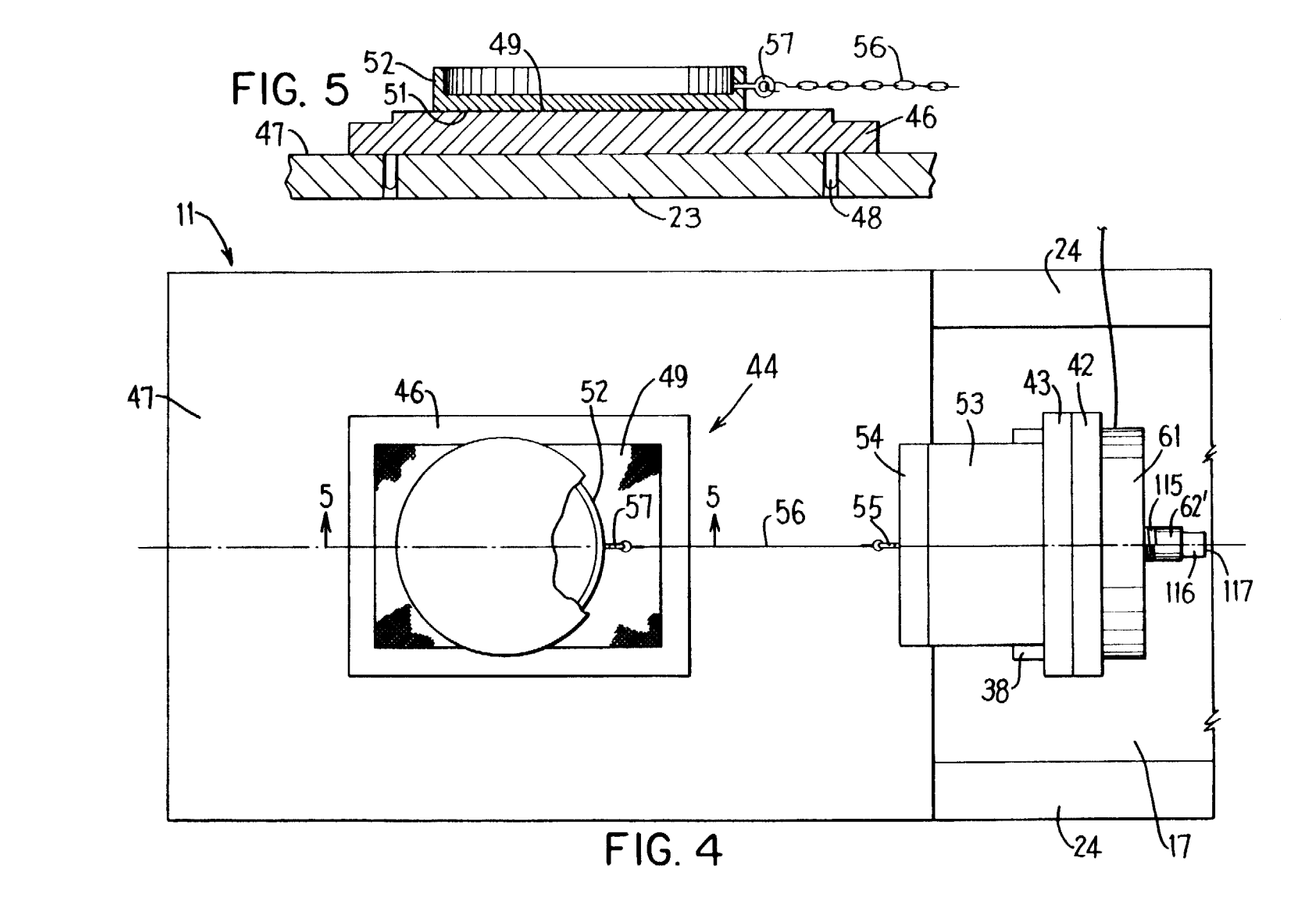
FIG. 4 is a fragmentary top view of the load module.
FIG. 5 is a fragmentary, sectional, elevational view of the assembly used for testing powder flow properties.

The load module 11, as illustrated by FIGS. 2-4, includes a boxlike housing 16, the leftward end of which defines a substantially enclosed compartment 16A whereas the rightward end defines a generally open compartment 16B. This housing 16 includes a base wall 17 which extends between and is rigidly joined to opposed vertically-extending end walls 18 and 19. An intermediate upright wall or partition 21 extends in parallel relationship approximately midway between the end walls for effecting separation between the closed and open compartments. The sides of the leftward compartment 16A are closed by suitable removable side walls 22. This leftward compartment 16A is closed at the upper extremity thereof by a generally horizontally extending top wall 23 which rigidly extends between and joins to the end wall 19 and the intermediate wall 21. The housing also includes a pair of upper frame rails 24 which are disposed on opposite sides of the open compartment 16B and extend horizontally between the end wall 18 and the intermediate wall 21 for rigid connection therewith. Other than these upper side rails 24, however, the top and sides of the rightward compartment 16B are otherwise open and the interior thereof is both visible and accessible.

Positioned within the interior of the closed compartment 16A is a precision drive unit 31 which includes a microstepping motor 32, preferably a low voltage direct current motor, drivingly coupled to a linear drive cylinder 33 through an intermediate speed reducer such as a belt drive 34. The linear drive cylinder 33 includes a housing in which is linearly slidably supported a ram 35, which ram is coupled through a precision nut-screw arrangement (such as an Acme screw) to a concentric rotatable shaft which is driven from the stepping motor 32 via the belt drive 34. The stepping motor 32 incorporates microstepping technology, such as by being coupled to a conventional motor control unit 36 so that, particularly when controlled from the computer 12, it is capable of moving a large number of steps per revolution such as from about 2,000 to about 25,000 steps per revolution. This drive arrangement provides for precise and fine control over both the velocity and the position of the movable ram 35.

The drive unit 31, namely the combination of the stepping motor 32 and the linear cylinder 33, is a known commercial unit, and in particular is manufactured by Industrial Devices Corporation of Novato, Calif.

The receptacle ram 35 slidably projects horizontally outwardly through the intermediate partition 21 so that the end thereof is positioned within the open compartment 16B, with the ram 35 being linearly movable substantially along the horizontal centerline 37. The ram 35, adjacent the free end thereof, fixedly mounts a vertically oriented guide plate 38 which projects downwardly therefrom and has a suitable ball-type slide bearing 39 extending therethrough, the latter slidably accommodating a horizontally elongate guide rod 41 which extends fixedly between the end plate 18 and the intermediate partition 21 in generally parallel relationship to the centerline 37. A support plate 42 is fixed to and projects upwardly from the guide plate 38 so as to project upwardly between and above the spaced side rails 24. The upper portion of this support plate 42 mounts thereon an adaptor block 43, which block couples to a powder flow testing assembly 44.

This powder flow testing assembly 44 includes a platelike shear cell table 46 which removably but stationarily attaches to the flat upper surface 47 of the top frame member 23. For this purpose, the shear cell table 46 has a plurality of small pins 48 projecting downwardly therefrom and adapted for reception within similarly-sized openings formed in the top wall 23. This shear cell table 46 defines thereon, an upper surface 49 which is suitably roughened, such as by machining shallow perpendicularly extending grooves therein. A similar roughened surface is formed on the bottom 51 of a shear cell sled 52, the latter being adapted to freely rest directly on the bed surface 49. The interior of the sled 52 is preferably hollowed out so as to accept additional weights if desired. The surface 49 of the shear bed is adapted to have a thin layer of powder deposited thereon, and the sled is then adapted to be positioned over but directly on the powder layer.

To effect movement of the sled 52 relative to the table 46, the flow determination assembly 44 includes a low-force strain-type transducer (i.e., load cell) 53 coupled to and projecting in cantilevered relationship away from the adaptor block 43. The other or cantilevered free end of the transducer 53 mounts thereon a coupling plate 54 which can be suitably vertically slidably adjusted relative to the transducer. This plate 54 in turn carries thereon a eye hook 55 which releasably couples to a suitable open hook provided on one end of a flexible tow line 56 (such as a cable or chain). This tow line 56 has a further open hook on the other end thereof which releasably couples to a further eye hook 57 provided on the sled 52.

The transducer 53 is designed specifically for recording low thrust forces, for example being a five-pound capacity load cell. The output from the load cell is suitably coupled to the computer 12 and/or the recording or plotting device 14 as diagrammatically illustrated in FIG. 1.

A further high-force strain-type transducer (i.e., load cell) 61 is coupled to the support 42 in coaxial alignment with the ram 35. This load cell 61 is disposed downstream of (i.e., forwardly of) the support plate 42 so that the load cells 53 and 61 are not coupled in series. This load cell 61 is sized to handle significantly greater forces than that possible with the load cell 53. For example, load cell 61 is preferably of about 1,000 pounds capacity.

Figure 11:
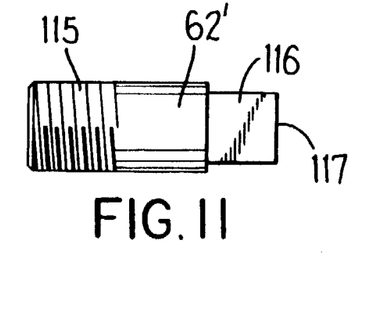
FIG. 11 illustrates the movable platen which attaches to the load module when conducting a tensile strength test using the assembly of FIGS. 8-10.

The load cell 61 has a central threaded opening for accommodating the threaded end of a removable ram element 62 (FIG. 2) or 62' (FIG. 11). The ram element 62 includes a generally spherical ball 63, such as a ball of about one-inch diameter, on the free end thereof in alignment with the axis 37. This ball 63 is utilized for creating a depression in a test tablet when testing for quasi-static hardness. Conversely, the ram element 62 can be removed and replaced by the ram element 62' of FIG. 11, which ram element 62' is described in greater detail hereinafter and is used for tensile strength testing.

To permit testing for quasi-static hardness of a tablet compressed of pharmaceutical powders, the load module 11 includes a tablet supporting assembly 65 (FIGS. 6 and 7) which is removably positionable within the open compartment 16B directly adjacent the inner surface 66 of end plate 18 so as to position a tablet T for cooperation with the ram ball 63.

Figure 6:
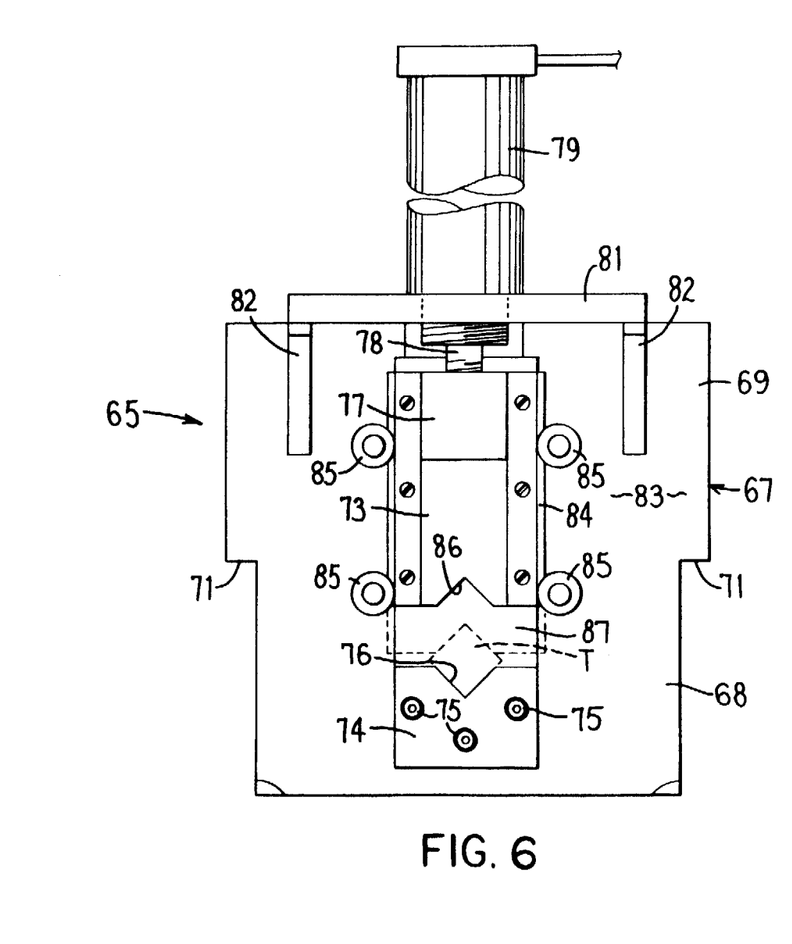
FIG. 6 is a front elevational view of a tablet support assembly used for testing quasi-static hardness.
Figure 7:
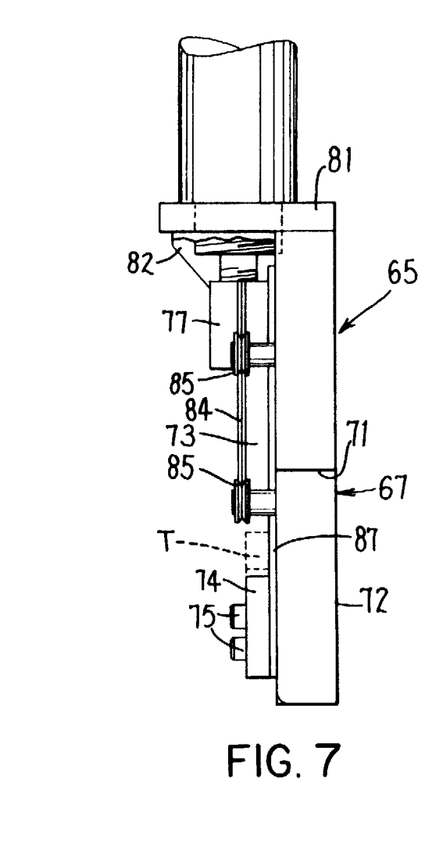
FIG. 7 is a side elevational view of the assembly shown in FIG. 6.

This tablet support assembly 65, herein referred to as the hardness head assembly, includes a generally T-shaped platelike support 67 which is generally vertically oriented and has a base portion 68 having a width which is slightly less than the sideward spacing between the top rails 24 so as to be freely but snugly vertically slidably accommodated therebetween. This base portion 68 is integrally joined to a head portion 69 which is of increased width in that it projects outwardly beyond the opposite side edges of the base portion 68 so as to define downwardly facing shoulders 71 which are adapted to supportingly bear against upper surfaces of the top rails 24. This support 67 also has a generally flat rear surface 72 which is adapted to directly overlie the inner surface 66 of the end plate 18. Hence, the T-shaped support 67 can be vertically slidably inserted downwardly between the top rails 24 so as to directly abut against the inner surface of the end plate 18, with the shoulders 71 bearing against the top rails 24.

Support plate 67 mounts thereon upper and lower tablet holders 73 and 74 respectively, the former being supported for vertical displacement to permit a known tablet or compact T to be held therebetween. In the illustrated embodiment, the lower tablet holder 74 is fixedly secured, as by screws 75, to the lower portion of the support plate 67 and projects outwardly from the front surface thereof. This lower tablet holder 74 has an upper edge which is spaced slightly below a horizontal plane containing the longitudinal axis 37 of the ram when the head assembly 65 is mounted on the load module, and a generally V-shaped tablet support notch 76 opens downwardly from the upper edge of the lower tablet holder. The side walls of this notch 76 define a generally 90° angle therebetween so as to accommodate one corner of the conventional tablet T.

The upper tablet holder 73 is supported for vertical slidable displacement on the support 67, and for this purpose the upper portion of tablet holder 73 has an adaptor plate 77 fixed to the front side thereof, the latter being coupled to the free end of a piston rod 78 which vertically slidably projects downwardly from a fluid pressure cylinder 79, normally an air cylinder. To support the air cylinder 79, the support plate 67 has a small platelike support 81 fixed to an upper edge thereof and projecting horizontally forwardly therefrom, the latter being additionally supported by a pair of sidewardly-spaced brackets 82 which secure the underside of support 81 to the front surface 83 of the support 67. The pressure cylinder 79 has the housing thereof fixedly mounted on the support 81 so that the cylinder projects upwardly therefrom. The upper end of the cylinder is connected to a source of pressurized air in a conventional manner so as to provide for controlled vertical displacement of the piston rod 78 and of the upper tablet support 73.

The upper tablet support 73 has guide ribs 84 extending vertically along opposite side edges thereof, which ribs are engaged with suitable guide rollers 85, such as V-shaped guide rollers, which are rotatably supported from the support 67 and rollingly engage opposite sides of the upper tablet holder 73.

The upper tablet upper holder 73 also has a V-shaped notch 86 opening upwardly through the bottom edge thereof, which notch defines a 90° angle and is substantially identical in size and configuration to the notch 76 formed in the lower tablet holder.

To facilitate vertical slidable displacement of the upper tablet holder 73 and additionally provide a proper backing for the tablet which is confined in the opposed notches 76, 86, there is provided a thin stainless steel support plate 87 which is fixed to the support 67 and is interposed between the front side thereof and the rear sides of the tablet holders 73 and 74.

When the hardness head assembly 65 is mounted on the load module 11, the T-shaped support 67, as depicted by dotted lines in FIGS. 2 and 3, is disposed so as to directly overlie the end surface 66 of the end plate 18, and is securely held thereagainst by a pair of pressure arm assemblies 88 which are mounted adjacent the opposite upper corners of the load module. Each of the pressure arm assemblies 88 includes an elongate lever-like pressure arm 89 which is disposed directly adjacent the inner vertical side of the respective top rail 24, with the upper end of the arm 89 being joined to the top rail by a suitable horizontal hinge 91. The lower end of the pressure arm has a transversely extending pin 92 which connects to one end of a tension spring 93, the other end of which is connected to an anchor 94 provided on the side edge of the end plate 18. The pressure arm 89 has a convexly curved clamping surface 95 defined along one side thereof so as to be disposed in opposed relationship to the end plate 18 whereby the spring 93 always resiliently urges this clamping surface 95 toward the end plate 18. When the hardness head assembly 65 is inserted into the load module 11, the support 67 thereof engages these clamping surfaces 95 and forces the levers 89 to swing in a counterclockwise direction against the urging of springs 93, whereby these clamping surfaces 95 are resiliently maintained in clamping engagement with the front surface 83 of the T-shaped support 67 to maintain it snugly in position and securely against the end plate 18.

Figures 8, 9:
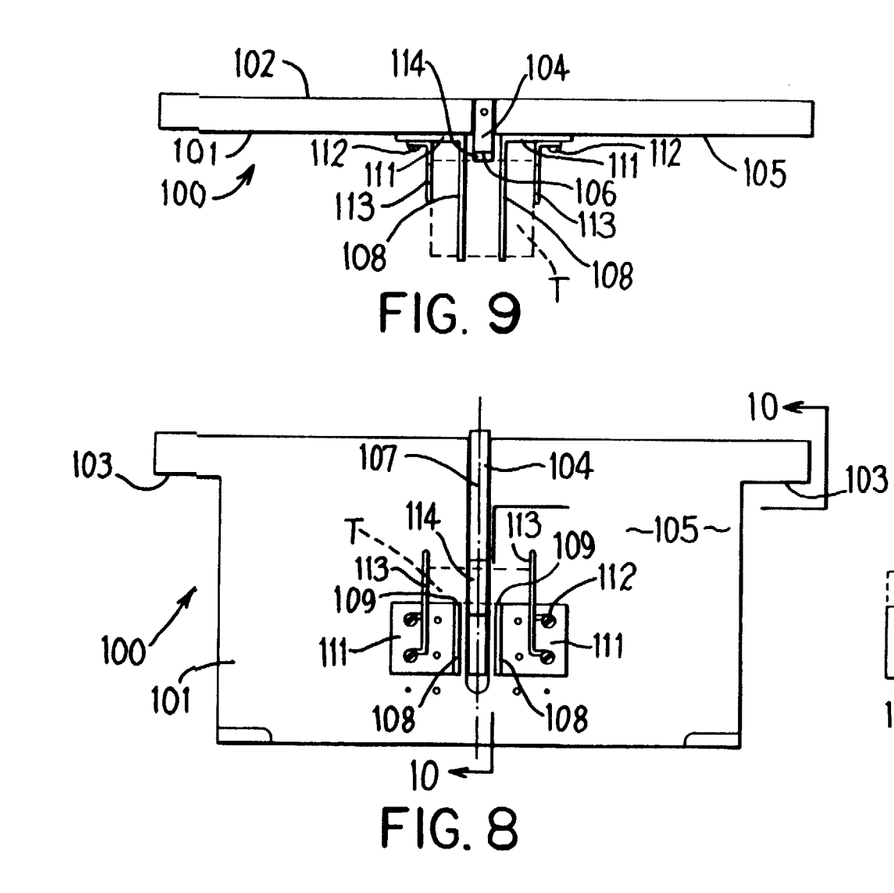
FIG. 8 is a front elevational view of a tablet support assembly for testing tensile strength.
FIG. 9 is a top view of the assembly shown in FIG. 8.
Figure 10:
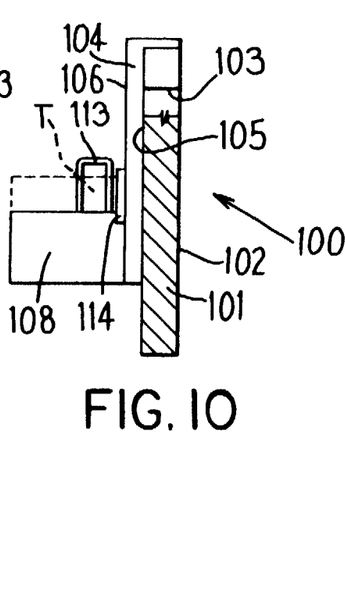
FIG. 10 is a side view of the assembly shown in FIG. 8.

When the load module 11 is to be used to test tensile strength, then there is utilized a tensile strength head assembly 100, as shown by FIGS. 8–10, for supporting the compact or tablet T. This head assembly 100 also includes a generally T-shaped platelike support 101 which is substantially identical to the support 67 associated with the hardness head assembly 65 except that the top portion of the support 101 is normally of lesser height. This support 101 is also sized so as to be snugly vertically accommodated between the top rails 24 of the frame and supported thereon by the downwardly facing shoulders 103 so as to permit the rear surface 102 to directly abut the housing end wall 18.

The T-shaped support 101 mounts thereon a vertically elongate platen or anvil 104 which is fixed to and projects outwardly from the front surface 105 of the support 101. This platen 104 defines thereon a vertically planar front face 106 which functions as an anvil surface for contact with a rear surface of a tablet T. The anvil 104 is disposed so that it is centered substantially along the vertical centerline 107, which centerline perpendicularly intersects the ram centerline 37 when the head assembly 100 is mounted on the load module 11.

To support the tablet T, the head assembly 100 mounts thereon a pair of tablet support blades 108 which are fixed to and project in cantilevered fashion perpendicularly outwardly away from the wall 105 in straddling relationship to the platen 104. These tablets support blades 108 are generally parallel with one another and comprise vertical plates which are horizontally thin so as to have only small upper edges 109 which supportingly engage the bottom surface of the tablet T. These blades 108 support the tablet T so that the center of the front face of the tablet is substantially aligned with the longitudinal axis 37 of the ram. These blades 108, in the illustrated embodiment, preferably comprise one of the legs of generally L-shaped elements which have the other legs 111 thereof disposed so as to directly overlie the front face of the support 101 for fixed securement therewith by means of screws 112.

Each L-shaped blade member 108, 111 mounts thereon a cantilevered spring clip 113 which projects upwardly above the blade, whereby the pair of sidewardly-spaced spring clips 113 are disposed so as to resiliently engage opposite side surfaces of the tablet T to assist in holding it in position when supported on the blades 108. Each spring clip 113 comprises a generally vertically inverted U-shaped wire element which is spaced outwardly from the respective blade 108 and has the legs thereof projecting downwardly and suitably deformed so as to be anchored by the screws 112.

In the preferred embodiment, the anvil 104 is also preferably provided with a thin resilient cushioning pad 114 secured to the front face 106 thereof in the region of contact with the tablet T.

When the tensile strength head assembly 100 is utilized on the load module 11, then the hardness ram element 62 is removed and replaced by the tensile strength ram element 62' of FIG. 11. This tensile strength ram element 62' has a threaded connection 115 for enabling its connection to the transducer 61, but instead of possessing a ball 63, is instead provided with a platen 116 on the leading or nose end thereof. This platen 116 has a width which substantially equals the width of the opposed fixed platen 104, and defines thereon a generally vertically planar front platen surface 117 which is parallel with the platen surface 106 and is adapted to directly connect the front side face of the tablet T supported on the head assembly 100. This front platen surface 117 has a vertical extent which is greater than the vertical height of the tablet T so as to contact the side surface of the tablet over the full vertical extent thereof.

OPERATION

The operation of the testing apparatus will be briefly summarized to ensure a complete understanding thereof.

When it is desired to carry out a shear cell test so as to determine the powder flow properties, then a thin layer of powder is deposited on the roughened upper surface 49 of the shear bed 46. The shear sled 52 is then positioned over the powder layer so that the powder layer is disposed between the opposed roughened surfaces 49 and 51. The shear sled 52 is coupled to the load cell 53 through the tow element 56. The control parameters and the start signal are then inputted to the control unit 36 of the force module 11 from the computer 12, whereby the stepping motor 32 is energized to effect a precise linear displacement of the ram 35, which in turn causes a corresponding movement of the support 42 which is coupled to one end of the load cell 53. During the test, the output from the load cell 53 is suitably supplied to the computer 12 and/or the recording device 14.

As the ram 35 is precisely displaced in extremely small increments by the stepping motor 32, a force or strain is imposed on the tow line 56 as caused by the frictional forces within the layer of powder, which forces initially tend to resist movement of the sled 52. This horizontal strain as imposed on the sled by the tow line, and the weight of the sled 52 which is imposed downwardly on the powder layer, tend to cause consolidation of the particles of powder in the layer. A shear force is applied to the powder layer due to the strain imposed on the sled by the tow line, and as this shear force increases, it reaches the point where it exceeds the frictional force in the powder layer and hence results in sideward movement of the sled 52. This causes the strain in tow line 56 and as imposed on the load cell 53 to drop significantly, substantially to zero. Thus, by monitoring the output of the strain gauge 53 by means of the computer 12 and/or the plotting device 14, there is created a force/time pattern which resembles a saw tooth pattern in that the pressure gradually builds up until the powder shear is exceeded, at which time the pressure drops significantly until approaching zero, following which the test procedure is repeated several times until uniform values of powder shear are recorded.

When it is desired to do a quasi-static hardness test, then the hardness head assembly 65 is mounted on the load module 11 by slidably inserting the T-shape support 67 vertically downwardly between the top rails 24 until the shoulders 71 abut against the top rails so as to snugly retain the T-shape support 67 within the end of the open compartment 16B. As the T-shape support plate 67 is slid downwardly against the inner surface of the end plate 18, the pressure levers 89 are forced outwardly away from the end plate as the convex camming surfaces 95 thereon slidably engage the front face of the T-shape support, whereby the pressure arms 89 exert a clamping pressure against the T-shape support so as to hold it firmly against the end plate 18. The T-shape support is securely held in the desired position due to engagement of the shoulders 71 against the upper surfaces of the top rails 24.

With the head assembly 65 mounted on the load module 11, the test tablet T is then inserted into the bottom notch 76 in bearing engagement against the support plate 87 substantially as indicated by dotted lines in FIGS. 6 and 7. Cylinder 79 is then energized to move the top tablet support 73 downwardly until the tablet is engaged within the upper notch 86. Pressure is continuously maintained on the cylinder 79 so that the opposed clamping supports 73 and 74 maintain a substantially uniform clamping pressure on all four side surfaces of the tablet.

The computer 12 then transmits suitable start and control signals to the control unit 36 which activates the stepping motor 32 to cause controlled linear extension of the ram 35 so as to move the ram ball 63 into contact with the exposed front face of the tablet T substantially at the mid-point thereof. When the initial point of contact between the ball 63 and tablet occurs, such contact is sensed by the signal from the load cell 61. The computer then causes a predetermined number of rotary movement steps of the motor 32 to cause a corresponding linear advance of the ram so that the ball 63 creates a depression of predetermined depth in the front face of the tablet. Throughout the forward advance of the ball 63 and the creation of the depression in the tablet, the load cell 61 continuously transmits strain measurement signals to the computer 12 and/or the recording device 14 so as to provide for an accurate plot of the force characteristic required to create the depression. When the ram ball 63 is advanced to its predetermined depth of depression, then the motor 32 is stopped and the ball 63 is maintained in this fully extended position for a predetermined period of time, such as approximately 30 minutes, during which the force imposed on the ball 63 is continuously monitored by the load cell 61. In fact, it is the force measurement which exists at the end of the dwell (i.e., compression), namely the relaxed force, which is used for calculating the quasi-static hardness of the tablet. This hardness is calculated using not only the final relaxed force measured during the test as described above, but also by measuring the dent chordal radius using a surface analyzer after removal of the tablet from the hardness head assembly.

When a determination of tensile strength is desired, then the hardness head assembly 65 and ram element 62 are removed and respectively replaced by the tensile strength head assembly 100 and ram element 62'. A tablet T is then positioned on the upper edges 109 of the blades 108, with the tablet being held between the opposed spring fingers 113. The tablet is oriented with its square cross section oriented upwardly, whereby a rear side surface of the tablet has a central portion thereof abutted against the stationary platen surface 106 (preferably with the cushion strip 114 interposed therebetween), and the front side surface of the tablet is thus oriented for contact with the end surface 117 of the ram element 62'. As in the hardness test, the computer 12 inputs start and control signals to the stepping motor 32 which advance the ram 35 until the platen surface 117 contacts the opposed side face of the tablet, as indicated by a measurement signal emitted from the force transducer 61, whereupon the tablet is stationarily held between the opposed platens 116 and 104. The continual energization of the motor 32 causes the ram to further forwardly advance and hence impose a significant force against the front face of the tablet to cause fracturing thereof. During this time, the force (i.e., strain) values are continuously transmitted from the transducer 61 to the computer and/or recording device and, in conjunction with the known displacement characteristic of the ram, enable a determination of the tensile strength of the tablet.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an apparatus for testing the physical properties of pharmaceutical powders, said apparatus including a frame, a ram movably supported on said frame for generally linear movement, a tablet support assembly positioned on said frame for supporting a blocklike tablet of compressed pharmaceutical powder in alignment with said ram for selective contact therewith, and drive means coupled to said ram for effecting linear displacement thereof, comprising the improvement wherein said drive means includes a microstepping rotary drive motor drivingly coupled to said ram through a rotary-to-linear motion converting device for causing linear movement of said ram in discrete steps, a first high-force load cell mounted on and coupled to said ram so that compressive forces imposed on said ram when engaged with the blocklike tablet are registered by said first load cell, a second low-force load cell supported on said ram for movement therewith, and a powder flow testing assembly coupled to said second load cell for testing and measuring flow shear properties of a pharmaceutical powder.

2. In an apparatus for testing the physical properties of pharmaceutical powders, said apparatus including a frame, a ram movably supported on said frame for generally linear movement, a tablet support assembly positioned on said frame for supporting a blocklike tablet of compressed pharmaceutical powder in alignment with said ram for selective contact therewith, and drive means coupled to said ram for effecting linear displacement thereof, comprising the improvement wherein said drive means includes a microstepping rotary drive motor drivingly coupled to said ram through a rotary-to-linear motion converting device for causing linear movement of said ram in discrete steps, and said ram includes a slidable ram member which projects outwardly in a cantilevered manner from said motion converting device, a first high-force load cell mounted on said ram member adjacent a free end thereof, a tablet-containing ram element coupled to said load cell in alignment with said ram member so that compressive forces imposed on said tablet-contacting ram element are registered by said first load cell, a support member fixed to said ram upstream of said first load cell and projecting transversely away from a centerline of said ram, a second low-force load cell coupled to said support member in sidewardly-spaced relationship from said ram, and a powder flow testing assembly coupled to said second load cell for testing and measuring flow shear properties of a pharmaceutical powder, said powder flow assembly including a bed stationarily supported on said frame and defining thereon an upwardly facing support surface on which a layer of powder is deposited, and a shear sled supported by gravity on said layer of powder and interconnected to said second load cell.

3. An apparatus according to claim 2, including first and second said tablet support assemblies removably and interchangeably positionable on said frame for respectively permitting testing of tablet hardness and tensile strength, each said tablet support assembly including a platelike support member which is vertically slidably insertable into said frame for deposition in direct supportive engagement with an adjacent upright frame wall so that forces imposed on a tablet by the ram are transmitted directly through the support member to the upright frame wall, and spring-urged pressure arms mounted on said frame for holding engagement with the respective support member for maintaining it in abutment against the upright frame wall.

4. An apparatus according to claim 3, wherein the frame includes a base plate which is secured to said upright frame wall and a pair of sidewardly-spaced top rails which are positioned upwardly from said base plate and are fixed to said upright frame wall and project generally perpendicularly away therefrom, the frame defining a compartment located forwardly of said upright frame wall and generally between said top rails with said compartment being freely accessible from opposite sides and from the top except for the presence of said top rails, and said support member comprising a generally T-shape plate which is vertically slidably inserted downwardly into the compartment so as to be disposed directly adjacent an inner surface of said upright frame wall, said T-shape plate being disposed so that a wider head portion thereof horizontally overlaps and is vertically supported on said sidewardly-spaced top rails.

5. An apparatus according to claim 4, wherein said shear sled is interconnected to the second load cell by an elongate tension member which extends approximately horizontally in generally parallel relationship with the centerline of the ram.

6. An apparatus to claim 1, wherein the microstepping motor is operable within a range of about 2,000 to about 25,000 steps per revolution.

7. An apparatus for testing physical properties of pharmaceutical powders, comprising:

a frame arrangement defining a generally closed first compartment and a generally open second compartment disposed in horizontally adjacent relationship to one another, said frame arrangement including a horizontally enlarged base plate fixed to generally parallel and vertically upwardly projecting end and intermediate plates which generally define said open compartment therebetween, said frame arrangement also including a pair of sidewardly-spaced frame rails which are spaced upwardly from said base plate and extend generally horizontally between and are fixedly joined to said intermediate and end walls, said open compartment being substantially freely accessible from the top and opposite sides thereof;

a ram arrangement supported for generally linear movement along a substantially horizontally-extending centerline which substantially perpendicularly intersects said upright end wall, said ram arrangement being partially positioned within said closed compartment and slidably projecting through said intermediate wall so as to project in cantilever fashion into said open compartment;

drive means positioned within said closed compartment and coupled to said ram arrangement for effecting linear displacement of said ram along said centerline in a microstepping manner, said drive arrangement including a microstepping rotary motor drivingly coupled to said ram arrangement through a rotary-to-linear motion converting device;

first means supported on said frame arrangement and cooperating with said ram arrangement for permitting testing of a blocklike tablet formed of compressed pharmaceutical powder, said first means including a support arrangement for stationarily supporting the blocklike tablet within said open compartment directly adjacent said upright end wall in substantial alignment with the centerline of said ram arrangement, said first means also including a first load cell for registering the forces imposed on the tablet by the ram arrangement; and second means supported on said frame arrangement and cooperating with said ram arrangement for testing the flow properties of a layer of pharmaceutical powder, said second means including a bed arrangement stationarily supported on said frame arrangement and defining thereon an upwardly-facing surface on which a thin layer of powder is deposited, a sled arrangement supported on the bed arrangement with the thin layer of powder interposed therebetween, the sled arrangement being disposed for movement in generally parallel relationship with the centerline of the ram arrangement and being drivingly interconnected to the ram arrangement, and a second load cell for registering the forces imposed on the sled arrangement by the ram arrangement, said second load cell being of substantially smaller force recording capability then said first load cell.

8. An apparatus according to claim 7, wherein said frame arrangement includes a top wall which extends over said closed compartment, said bed arrangement being stationarily mounted on said top wall, said second means including a support which is disposed within said open compartment and is fixed to said ram arrangement, said support projecting transversely of said ram upwardly between said sidewardly-spaced top rails, said second load cell being fixed to said support adjacent an upper free end thereof and projecting generally toward said intermediate wall, and a generally horizontally elongate tension element coupled between said second load cell and said movable sled member.

9. An apparatus according to claim 7, wherein said first means includes a removable tablet-supporting head assembly provided with a generally vertically-enlarged T-shaped support plate having a generally vertically enlarged back surface adapted to substantially abut an inner surface of said end wall, and tablet support means mounted on said support plate adjacent a front surface thereof for stationarily supporting the blocklike tablet, the T-shaped support plate being vertically slidably insertable downwardly between said sidewardly-spaced frame rails so that said T-shaped support plate substantially directly abuts the inner surface of said upright end wall, said T-shaped support plate having upper portions which project sidewardly in opposite directions so as to overlie and be vertically supported on said side frame rails.

10. An apparatus according to claim 9, including pressure means positioned for vertical slidable engagement with a front face of said T-shaped support plate while horizontally urging said support plate backwardly against said end wall.

11. An apparatus according to claim 10, wherein said pressure means includes a pair of pressure arms which are respectively disposed adjacent and pivotally supported on the side frame rails, each said pressure arm having a rearward curved surface adapted for slidable contact with the front face of the T-shaped support plate, and spring means cooperating with each of the pressure arms for swingably urging the pressure arm toward the end wall so as to make pressure contact with the front face of the T-shaped support plate.

12. An apparatus according to claim 11, wherein said frame arrangement includes a top wall which extends over said closed compartment, said bed arrangement being stationarily mounted on said top wall, said second means including a support which is disposed within said open compartment and is fixed to said ram arrangement, said support projecting transversely of said ram upwardly between said sidewardly-spaced top rails, said second load cell being fixed to said support adjacent an upper free end thereof and projecting generally toward said . intermediate wall, and a generally horizontally elongate tension element coupled between said second load cell and said movable sled member.

13. An apparatus according to claim 9, wherein said first means includes a second tablet-supporting head assembly which is removably positionable on said frame and interchangeable with said first-mentioned head assembly, said second head assembly having a T-shaped support plate which mounts on the frame arrangement in the same manner as the T-shaped support plate of the first head assembly, said second head assembly having a tablet support structure associated therewith for supporting the blocklike tablet in a different orientation from that of said first head assembly.

14. An apparatus according to claim 13, wherein said ram arrangement includes a tablet-contacting ram head removably coupled to the free end thereof, and said first load cell being interposed between said removable ram head and the remainder of the ram arrangement.

15. An apparatus according to claim 14, wherein said frame arrangement includes a top wall which extends over said closed compartment, said bed arrangement being stationarily mounted on said top wall, said second means including a support which is disposed within said open compartment and is fixed to said ram arrangement, said support projecting transversely of said ram upwardly between said sidewardly-spaced top rails, said second load cell being fixed to said support adjacent an upper free end thereof and projecting generally toward said intermediate wall, and a generally horizontally elongate tension element coupled between said second load cell and said movable sled member.

16. An apparatus according to claim 9, wherein said frame arrangement includes a top wall which extends over said closed compartment, said bed arrangement being stationarily mounted on said top wall, said second means including a support which is disposed within said open compartment and is fixed to said ram arrangement, said support projecting transversely of said ram upwardly between said sidewardly-spaced top rails, said second load cell being fixed to said support adjacent an upper free end thereof and projecting generally toward said intermediate wall, and a generally horizontally elongate tension element coupled between said second load cell and said movable sled member.

17. An apparatus for testing physical properties of pharmaceutical powders, comprising:
  a frame arrangement;
  a ram arrangement movably supported on said frame arrangement for generally linear movement along a substantially horizontally-extending centerline, said ram arrangement including a horizontally cantilevered ram member;
  first and second load cells mounted on said ram member for movement therewith, said first load cell being of substantially greater force-transmitting capacity than said second load cell, said first load cell being coaxially mounted on said ram member adjacent a free end thereof, and said second load cell being mounted on said ram arrangement in sidewardly-spaced relationship from said centerline so as to be independent of said first load cell;
  said ram arrangement also including a tablet contacting ram element removably coupled to said first load cell;
  first and second tablet-supporting head assemblies removably and alternatively positionable on said frame arrangement for respectively permitting testing of tablet hardness and tensile strength, said first and second head assemblies respectively including first and second tablet supporting means for removably supporting a tablet in a position wherein it is aligned with the centerline of the ram arrangement when the respective head assembly is mounted on the frame arrangement, said first and second tablet supporting means orienting the tablet in respective first and second positions which are different;

a powder flow test assembly mounted on said frame arrangement for operative connection to said second load cell for testing and measuring the flow shear properties of pharmaceutical powder, said powder flow test assembly including a bed stationarily supported on said frame arrangement and defining thereon an upwardly-facing support surface on which a layer of powder is deposited, and a sled member supported by gravity on said layer of powder and movable horizontally therealong, said sled being interconnectable to said second load cell; and drive means for effecting linear displacement of said ram arrangement along said centerline in a microstepping manner, said drive arrangement including a microstepping rotary motor coupled to said ram arrangement through a rotary-to linear motion converting device, and control means connected to said motor for causing said motor to operate in an operating range having a lower limit of about 2,000 motor steps per revolution.

18. An arrangement according to claim 17, wherein said frame arrangement and each of said head assemblies includes cooperating means which enables each head assembly to be vertically slidably positioned on and supportingly engaged with said frame arrangement when a tablet test is to be conducted, and spring-biased pressure means cooperating between said frame arrangement and the respective head assembly for maintaining the head assembly properly positioned on the frame arrangement during the test.

* * * * *

UNITED STATES PATENT AND TRADEMARK OFFICE
CERTIFICATE OF CORRECTION

PATENT NO. : 5 140 861

DATED : August 25, 1992

INVENTOR(S) : David D. Gleason et al

It is certified that error appears in the above-identified patent and that said Letters Patent is hereby corrected as shown below:

Item [57] ABSTRACT;
   line 7; change "mount of" to ---mount on---.

Column 11, lines 31-32; change "tablet-containing" to
         ---tablet-contacting---.

Column 13, line 34; delete the period after "surface".

Signed and Sealed this

Fifth Day of October, 1993

Attest:

BRUCE LEHMAN

Attesting Officer     Commissioner of Patents and Trademarks